United States Patent
Doffing et al.

(10) Patent No.: US 7,075,777 B2
(45) Date of Patent: Jul. 11, 2006

(54) METHOD AND APPARATUS FOR A CAPACITOR SHELL INCLUDING TWO MATEABLE CUPPED COMPONENTS

(75) Inventors: Brian Doffing, Roseville, MN (US); James A. Taller, White Bear Lake, MN (US); Gregory J. Sherwood, North Oaks, MN (US); Jason A. Shiroff, Shoreview, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 0 days.

(21) Appl. No.: 11/124,705

(22) Filed: May 9, 2005

(65) Prior Publication Data

US 2006/0012945 A1 Jan. 19, 2006

Related U.S. Application Data

(60) Provisional application No. 60/588,905, filed on Jul. 16, 2004.

(51) Int. Cl.
*H01G 2/10* (2006.01)
*H01G 9/10* (2006.01)

(52) U.S. Cl. ..................... 361/517; 361/535
(58) Field of Classification Search ........ 361/516–521, 361/535–539, 502; 607/5
See application file for complete search history.

(56) References Cited

U.S. PATENT DOCUMENTS

| | | | |
|---|---|---|---|
| 4,243,042 A | 1/1981 | Ware | |
| 4,385,342 A | 5/1983 | Puppolo et al. | |
| 4,659,636 A | 4/1987 | Suzuki et al. | |
| 4,882,115 A | * | 11/1989 | Schmickl .................. 361/538 |
| 5,131,388 A | 7/1992 | Pless et al. | |
| 5,370,663 A | 12/1994 | Lin | |
| 5,439,760 A | 8/1995 | Howard et al. | |
| 5,456,698 A | 10/1995 | Byland et al. | |
| 5,522,851 A | 6/1996 | Fayram | |
| 5,645,586 A | 7/1997 | Meltzer | |
| 5,674,260 A | 10/1997 | Weinberg | |
| 5,716,729 A | 2/1998 | Sunderland et al. | |
| 5,930,109 A | 7/1999 | Fishler | |
| 6,004,692 A | 12/1999 | Muffoletto et al. | |
| 6,225,778 B1 | 5/2001 | Hayama et al. | |

(Continued)

FOREIGN PATENT DOCUMENTS

JP 2-266508 * 10/1990

(Continued)

OTHER PUBLICATIONS

Dombro, Ron, "Method and Apparatus for Insulative Film for Capacitor Components", U.S. Appl. No. 11/124,792, filed May 9, 2005, 44 Pages.

(Continued)

Primary Examiner—Eric W. Thomas
(74) Attorney, Agent, or Firm—Schwegman, Lundberg, Woessner & Kluth, P.A.

(57) ABSTRACT

One embodiment of the present subject matter includes a capacitor, comprising a first cupped shell having a first opening, and a second cupped shell having a second opening, wherein the first opening and the second opening are adapted to sealably mate to form a closed shell defining a volume therein. In the embodiment, the closed shell is adapted for retaining electrolyte. A plurality of capacitor layers in a substantially flat arrangement are disposed within the volume, along with electrolyte, in the present embodiment. The present closed shell includes one or more ports for electrical connections.

17 Claims, 5 Drawing Sheets

U.S. PATENT DOCUMENTS

| | | |
|---|---|---|
| 6,275,729 B1 | 8/2001 | O'Phelan et al. |
| 6,297,943 B1 | 10/2001 | Carson |
| 6,421,226 B1 | 7/2002 | O'Phelan et al. |
| 6,426,864 B1 | 7/2002 | O'Phelan et al. |
| 6,509,588 B1 | 1/2003 | O'Phelan et al. |
| 6,522,525 B1 | 2/2003 | O'Phelan et al. |
| 6,556,863 B1 | 4/2003 | O'Phelan et al. |
| 6,571,126 B1 | 5/2003 | O'Phelan et al. |
| 6,586,134 B1 | 7/2003 | Skoumpris |
| 6,610,443 B1 | 8/2003 | Paulot et al. |
| 6,613,474 B1 | 9/2003 | Frustaci et al. |
| 6,636,417 B1 * | 10/2003 | Sakata et al. ............... 361/502 |
| 6,687,118 B1 | 2/2004 | O'Phelan et al. |
| 6,699,265 B1 | 3/2004 | O'Phelan et al. |
| 6,801,424 B1 * | 10/2004 | Nielsen et al. ............... 361/517 |
| 6,850,405 B1 * | 2/2005 | Mileham et al. ............ 361/302 |
| 6,859,353 B1 * | 2/2005 | Elliott et al. ................. 361/517 |
| 2003/0017372 A1 | 1/2003 | Probst et al. |
| 2004/0031142 A1 | 2/2004 | Paulot |
| 2004/0039421 A1 | 2/2004 | O'Phelan et al. |
| 2004/0127952 A1 | 7/2004 | O'Phelan et al. |
| 2004/0147960 A1 | 7/2004 | O'Phelan et al. |
| 2004/0147961 A1 | 7/2004 | O'Phelan et al. |
| 2004/0220627 A1 | 11/2004 | Crespi et al. |
| 2005/0177193 A1 | 8/2005 | Nielsen et al. |

FOREIGN PATENT DOCUMENTS

| | | |
|---|---|---|
| JP | 02226508 | 10/1990 |
| WO | WO-00/19470 | 4/2000 |

OTHER PUBLICATIONS

Sherwood, Gregory J., "Method and Apparatus for High Voltage Aluminum Capacitor Design", U.S. Appl. No. 11/182,707, filed Jul. 15, 2005, 239 Pages.

Sherwood, Gregory J., "Method and Apparatus for Providing Flexible Partially Etched Capacitor Electrode Interconnect", U.S. Appl. No. 60/588,905, filed Jul. 16, 2004, 241 Pages.

* cited by examiner

METHOD AND APPARATUS FOR A CAPACITOR SHELL INCLUDING TWO MATEABLE CUPPED COMPONENTS

CROSS REFERENCE TO RELATED APPLICATIONS

The present application is related to the following commonly assigned U.S. Patents which are incorporated by reference in their entirety: "High-Energy Capacitors for Implantable Defibrillators," U.S. Pat. No. 6,556,863, filed Oct. 2, 1998, issued Apr. 29, 2003; "Flat Capacitor for an Implantable Medical Device," U.S. Pat. No. 6,699,265, filed Nov. 3, 2000, issued Mar. 2, 2004. Additionally, the present application is related to the following Provisional U.S. Patent Application which is assigned to the same assignee and is incorporated by reference in its entirety: "Method and Apparatus for Single High Voltage Aluminum Capacitor Design," Ser. No. 60/588,905, filed on Jul. 16, 2004. Additionally, the present application is related to the following commonly assigned copending U.S. patent application which is incorporated by reference in its entirety: "Heat Shrinkable Wrap for Capacitor," Ser. No. 11/124,792, filed on May 9, 2005.

TECHNICAL FIELD

This disclosure relates generally to capacitors, and more particularly, to a method and apparatus for a capacitor shell including two mateable cupped components.

BACKGROUND

There is an ever-increasing interest in making electronic devices physically smaller. Consequently, electrical components become more compact as technologies are improved. However, such advances in technology also bring about additional problems. One such problem involves packaging components in devices.

Packaging is especially problematic with components incorporating multiple layers. One such component is the capacitor. Capacitors provide improved charge storage and energy density using multiple conductive layers and advanced dielectrics. As the layers become more complex and smaller in dimensions, problems arise with packaging. Housings for complex shapes defining contoured layer stacks are needed.

Thus, there is a need in the art for housing designs which are adapted to new capacitor stack shapes, and which improve packaging efficiency without sacrificing substantial performance of the component.

SUMMARY

The above-mentioned problems and others not expressly discussed herein are addressed by the present subject matter and will be understood by reading and studying this specification.

In one embodiment, the present subject matter includes a capacitor, comprising: a first cupped shell having a first opening; a second cupped shell having a second opening, wherein the first opening and the second opening are adapted to sealably mate to form a closed shell defining a volume therein, the closed shell adapted to retain electrolyte; a plurality of substantially planar capacitor layers in a stacked arrangement disposed within the volume; and electrolyte disposed within the volume, wherein the closed shell includes one or more ports for electrical connections.

In one additional embodiment, the present subject matter includes a capacitor, comprising: a plurality of substantially planar capacitor layers in a stacked arrangement; a first shell means for partially housing the plurality of substantially planar capacitor layers; a second shell means sealably mated to the first shell means at a joint and defining a closed shell means and further defining a volume therein, the closed shell means for housing the plurality of substantially planar capacitor layers and for retaining electrolyte; and electrolyte disposed within the volume, wherein the plurality of substantially planar capacitor layers are disposed within the volume and the closed shell means includes one or more ports for electrical connections.

One additional embodiment of the present subject matter includes a method, comprising: positioning a plurality of substantially planar capacitor layers in a stacked arrangement in a first cupped shell having a first opening; sealably mating a second opening of a second cupped shell to the first opening of the first cupped shell along a joint, the mated first and second cupped shells defining a closed shell having a volume and at least one electrical port providing access to the volume; and disposing electrolyte in the volume.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references may contemplate more than one embodiment. The following detailed description is, therefore, not to be taken in a limiting sense, and the scope is defined only by the appended claims, along with the full scope of legal equivalents to which such claims are entitled.

In various embodiments, flat capacitors with stacked planar or substantially planar electrodes are used to power electronic devices. For example, flat capacitors are used in implantable medical devices such as implantable cardioverter defibrillators. Capacitors include anodes and cathodes, and in various embodiments, the anodes and cathodes are divided into interconnected layers.

In part, the nature of implantation and patient comfort requires ergonomically shaped devices for implantation. Ergonomic devices often have curved profiles. In the past, capacitors which are flat have consisted of rectangular structures. In creating ergonomic device housings which incorporate capacitors with rectangular shapes, space has been wasted, as is the case when a sphere is used to encapsulate a box.

In capacitor embodiments which are not rectangular, but have a curved profile, a different problem exists. Capacitor housings have been efficiently made using a deep-draw process to make a receiving cup, combined with a planar lid mateable to the cup opening. A capacitor with a curved profile can be placed in a deep drawn receiving cup with a curved bottom, using the space around the curved bottom reasonably well. Unfortunately, the deep drawn process is suited to create curves in only one direction. For example, forming a cup involves pushing a die against a plate. The die must then be removed from the plate. Such processes are not suited to create a unitary sphere shaped piece.

In order to enable capacitors with ovoid or sphere-shaped curves, the present subject matter includes, but is not limited to, embodiments with a shell comprised of two mateable cupped components. For example, a first cup shaped shell can be deep drawn. This example shell can conform to a curved component to be placed in it. The example also includes a second cup shaped shell, which also is deep drawn. This example second shell can conform to curved portions of a capacitor shape which are sticking out of the first shell. In this example, a capacitor stack with an ergonomic shape can be efficiently packaged using a two piece casing or shell. This benefit, as well as other benefits, is facilitated by the present subject matter.

Figure 1:
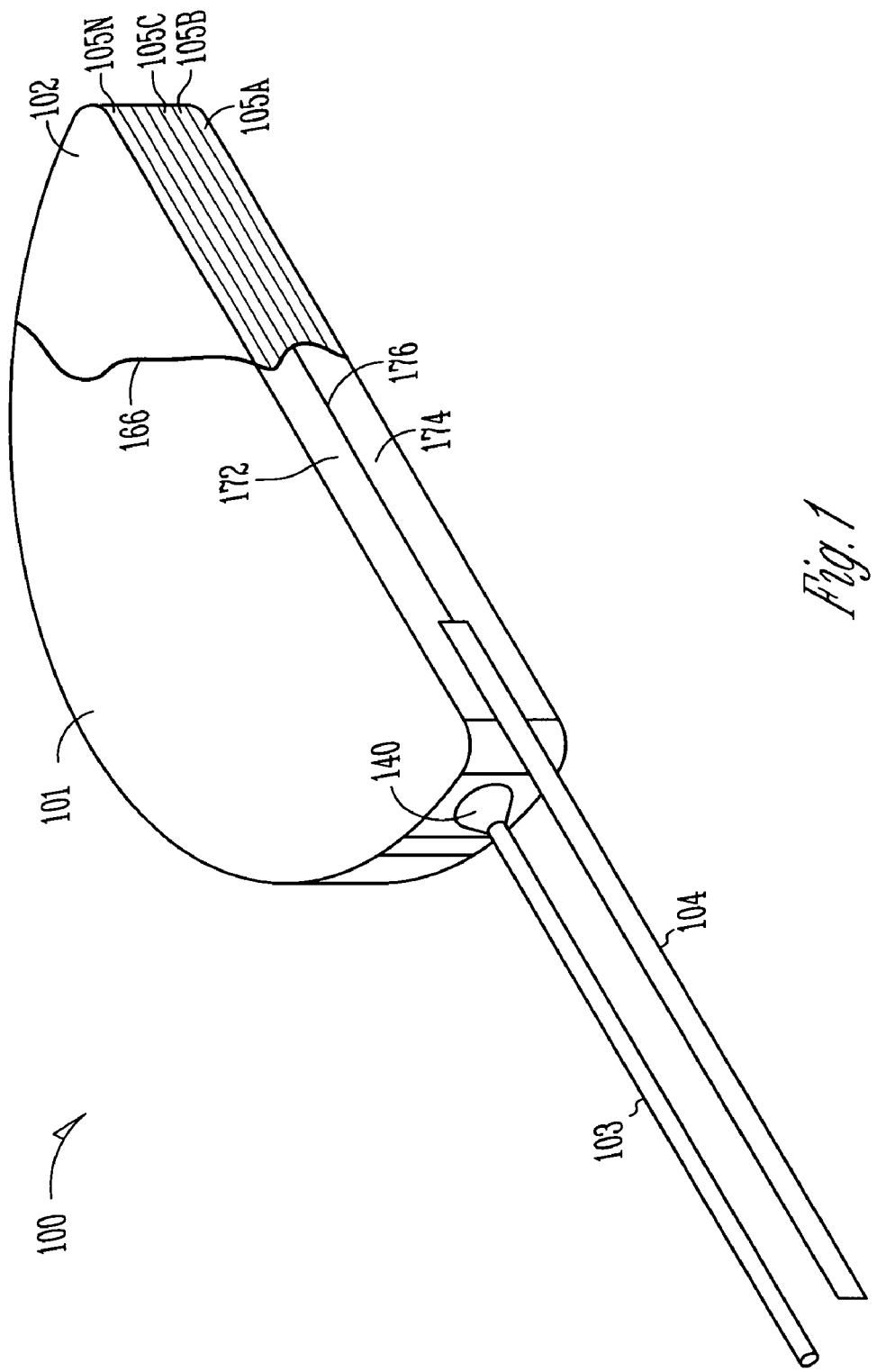
FIG. 1 is a perspective view of a capacitor with two cupped shells, according to one embodiment of the present subject matter.

FIG. 1 shows a flat capacitor 100 constructed according to one embodiment of the present subject matter. Although capacitor 100 is a D-shaped capacitor, in additional embodiments the capacitor is another desirable shape, including, but not limited to, rectangular, circular, oval or other symmetrical or asymmetrical shapes. Capacitor 100 includes a case 101 which contains a capacitor stack 102. In some embodiments, case 101 is manufactured from a conductive material, such as aluminum. In additional embodiments, the case 101 is manufactured using a nonconductive material, such as a ceramic or a plastic. The capacitor stack 102, in various embodiments, is constructed from planar anode, cathode, and separator subcomponents, as is discussed herein.

In various embodiments, the case 101 is divided into a first shell 172 and a second shell 174. In some embodiments, the first shell 172 and the second shell 174 are cup shaped and/or concave. First shell 172 and second shell 174 are mateable to one another, in various embodiments. In some embodiments, a seam or joint 176 is defined by the mated intersection of the first shell 172 and the second shell 174. Seam 176, in these embodiments, includes various types of known joints, including butt joints, step joints, and lap joints. The scope of joints in the present subject matter includes joints which are flush to the exterior before welding, joints which are flush to the exterior after welding, joints which are flush to the interior before welding, and joints which are flush to the interior after welding. In various embodiments, these joints start in a non-flush state and are made flush during welding, either by removing metal, or by adding filler metal. In some of these embodiments, joints which are flush in a beginning state are similarly adapted to become non-flush after welding.

Capacitor 100 includes a first terminal 103 and a second terminal 104 for connecting capacitor stack 102 to an outside electrical component, such as heart monitor circuitry, including defibrillator, cardioverter, and pacemaker circuitry. In one embodiment, terminal 103 includes a feedthrough terminal 140 insulated from case 101, while terminal 104 is directly connected to case 101. In additional embodiments, one, two, three or more feedthroughs are used. Terminal 103 comprises an aperture in one or more shells of the case, in various embodiments. Additionally, terminal 103 includes a seal in various embodiments. One embodiment of feedthrough 140 includes epoxy. The capacitor incorporates additional connection structures and methods in further embodiments. The present subject matter includes, but is not limited to, additional connection structures and methods illustrated on pages 12–13, 59–60, 63–82 of related and commonly assigned Provisional U.S. Patent Application, "Method and Apparatus for Single High Voltage Aluminum Capacitor Design," Ser. No. 60/588,905, filed on Jul. 16, 2004, incorporated herein by reference.

Capacitor stack 102 includes one or more cathodes, one or more separators, and one or more anodes. Additionally, in some embodiments, these components are organized into capacitor elements 105a, 105b, 105c, . . . , 105n, illustrated through break line 166. A capacitor element includes at least one anode layer, and at least one cathode layer. In various embodiments, multiple elements are interconnected. For example, in one embodiment a first element having a first anode layer is interconnected with a second element having a second anode layer, with the first anode layer and the second anode layer interconnected. In various embodiments, stack 102 is formed in two steps, including a first step of stacking capacitor components into two or more elements 105a, 105b, 105c, . . . , 105n, and a second step of stacking elements into a capacitor stack. Additional embodiments include forming a capacitor stack in a single step, or more steps. The present subject matter includes, but is not limited to, additional embodiments disclosed on pages 41–50 of related and commonly assigned Provisional Patent Application "Method and Apparatus for Single High Voltage Aluminum Capacitor Design," Ser. No. 60/588,905, filed on Jul. 16, 2004, which is incorporated herein by reference.

Each cathode of capacitor stack 102, in various embodiments, is a metallic planar structure. Varying examples include a cathode layer connected to an additional cathode layers using a variety of methods and structures, including welding. In some embodiments, the cathodes are coupled to conductive case 101, and terminal 104 is attached to case 101, providing a connection between the cathode and outside circuitry. In some embodiments, the cathode is coupled to a feedthrough assembly. In some embodiments, a feedthrough assembly includes a feedthrough conductor extending through a feedthrough hole. Configurations having multiple cathode feedthroughs are within the scope of the present subject matter.

Capacitor stack 102 additionally includes one or more anodes, in various embodiments. Anodes can include aluminum, tantalum, hafnium, niobium, titanium, zirconium, and combinations of these metals, in various embodiments. In one embodiment, at least portions of a major surface of each anode is roughened and/or etched to increase its effective surface area. This increases the capacitive effect of the anode on a volumetric basis.

In various embodiments, anode subcomponents are connected to other anode subcomponents of the capacitor anode, the connected subcomponents coupled to feedthrough assembly 103 for electrically connecting the anode to circuitry outside the case. In some embodiments, a feedthrough assembly includes a feedthrough conductor extending through a feedthrough hole. Configurations having multiple anode feedthroughs are within the scope of the present subject matter. In some embodiments, the anode is connected to the case and the cathode is coupled to one or more feedthrough assemblies. In various embodiments, both the anode and the cathode are connected to components through on or more feedthroughs.

In addition to cathodes and anodes, various embodiments include a separator positioned, in part, to insulate capacitor stack components. One or more separators are used to insulate anode subcomponents from cathode subcomponents, for example. In various embodiments, the separator includes one or more sheets of kraft paper impregnated with an electrolyte. Varying forms of electrolyte includes a fluidic compound adapted for use in a capacitor. Examples with electrolyte include any electrolyte for an electrolytic capacitor, such as an ethylene-glycol base combined with polyphosphates, ammonium pentaborate, and/or an adipic acid solute.

The present subject matter includes, but is not limited to, anodes, cathodes, separators, and additional components disclosed on pages 29–34 of related and commonly assigned Provisional U.S. Patent Application: "Method and Apparatus for Single High Voltage Aluminum Capacitor Design," Ser. No. 60/588,905, filed on Jul. 16, 2004, incorporated herein by reference.

Capacitor embodiments within the present subject matter include a capacitor stack adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

In various embodiments, the stack is disposed in a case, and linked with other components, a state which affects some of these values. For example, in one packaged embodiment, including a case and terminals, the energy density available ranges from about 5.3 Joules per cubic centimeter of capacitor stack volume to about 6.3 Joules per cubic centimeter of capacitor stack volume. Some embodiments are adapted to deliver about 5.8 Joules. In various embodiments, these ranges are available at a voltage of between about 410 volts to about 610 volts.

It should be noted that throughout the present application, matching numbers indicate similar features and/or functions. Matching numbers help to explain the subject matter, but the arbitrary nature of shapes, such as capacitor electrode shapes, is emphasized, and matching numbers are not to be interpreted as limiting.

Figure 2:
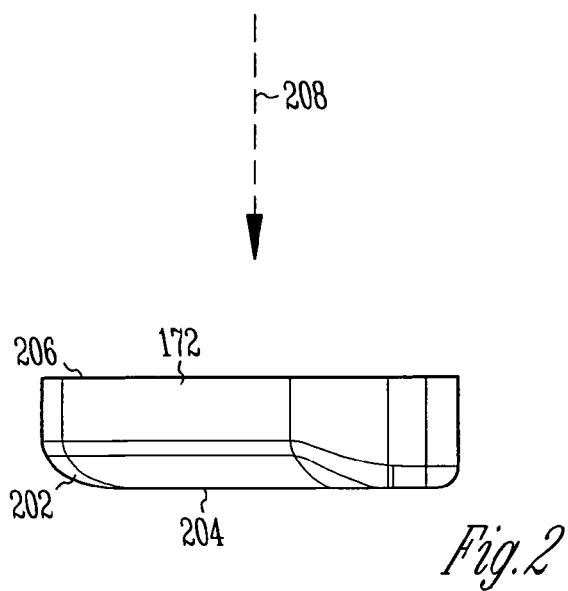
FIG. 2 is a top view of a capacitor case component, according to one embodiment of the present subject matter.

FIG. 2 is a top view of a capacitor case component, according to one embodiment of the present subject matter. First shell 172 includes a rounded portion 202. In various embodiments, a rounded portion such as rounded portion 202 extends to and defines a planar portion 204. The rounded portion 202 is useful for packaging in an ergonomic device housing. For example, in various embodiments, a capacitor comprised of first shell 172 is disposed in a device housing which has an ergonomic exterior. Some embodiments with an ergonomic exterior include a similarly shaped interior. The shape of first shell 172, including rounded portion 202, is adapted to mate to such an interior, in various embodiments.

First shell 172, in various embodiments, is cup shaped. Some cup shaped embodiments are formed using a deep draw process, as is known in the art. Deep drawing processes press a sheet of metal into a shape. The resulting shape includes first opening 206. Because one or more dies used during this process must be extracted, the shape of the first shell 172 is limited, in various embodiments. In deep draw embodiments which have dies extracted as such, along axis 208 for example, features of first shell 172 must not extend orthogonally further away from axis 208 than does material defining opening 206.

Figure 3:
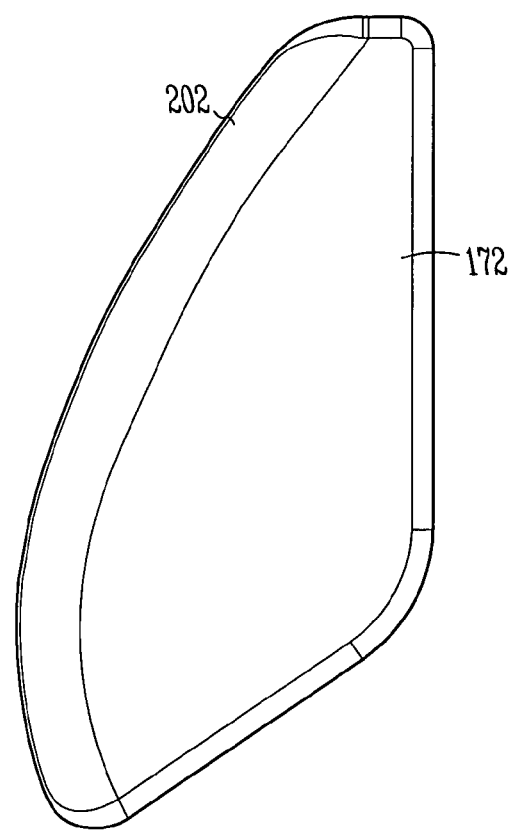
FIG. 3 is a front view of a capacitor case component, according to one embodiment of the present subject matter.

FIG. 3 is a front view of a capacitor case component, according to one embodiment of the present subject matter. Visible in the illustration is rounded portion 202 of first shell 172.

Figure 4:
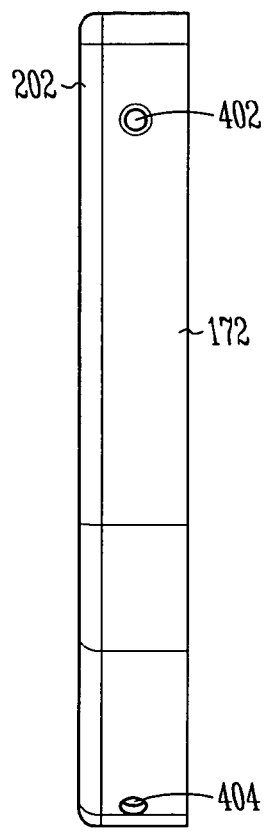
FIG. 4 is a side view of a capacitor case component, according to one embodiment of the present subject matter.

FIG. 4 is a side view of a capacitor case component, according to one embodiment of the present subject matter. In various embodiments, first shell 172 includes openings 402, 404. First opening 402, in various embodiments, is useful as an electrical port, such as a feedthrough, or as fill-port. A fill-port is used for filling a capacitor case with electrolyte, in various embodiments. Various additional uses including an aperture in first shell 172 are also within the scope of the present subject matter. Similarly, opening 404 is useful for a number of functions. In some of these embodiments, the openings 402, 404 include a step. A step is useful, in various embodiments, for reducing damaging laser refraction in embodiments which seal a plug to the openings using laser welding.

Opening 402 may be drilled, punched, or otherwise formed as is known in the art. In various embodiments, opening 402 is flush to the interior and exterior of first shell 172. In additional embodiments, opening 402 is not flush. Various embodiments include a bevel, or are otherwise adapted to provide functions known in the art. One embodiment extends into the volume defined by first shell 172 and second shell 174.

Figure 5:
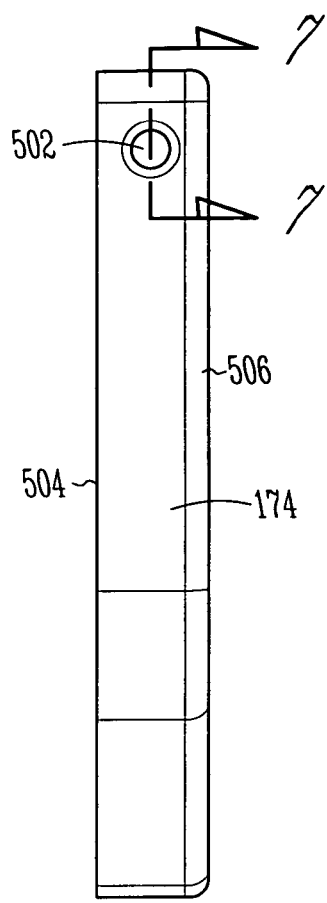
FIG. 5 is a side view of a capacitor case component, according to one embodiment of the present subject matter.

FIG. 5 is a side view of a capacitor case component, according to one embodiment of the present subject matter. In various embodiments, second shell 174 includes an opening 502. The design of second shell 174 can include features, such as rounded edges 506, to comply with ergonomic requirements, in various embodiments. Opening 502, in one embodiment, is adapted for use as a feedthrough. Some feedthrough designs, including embodiments of 502, include a wall which extends into the volume defined by first shell 172 and second shell 174. One embodiments of this design is described in portions of this application discussing FIG. 7.

It should be noted that the rectangular shape visible in the side-view of the second shell 174 should not be understood as limiting. Although the rectangular shape is adapted for housing a rectangular capacitor stack, comprised of layers of capacitor electrodes with similar edge profiles, other embodiments are within the scope of the present subject matter, including embodiments in which the second shell 174 has a hemispherical profile, a partially ovoid profile, or other profiles. Generally, these embodiments extend away from opening 504 with cross sections, viewed parallel to opening 504, of same or decreasing area. This is due, in various embodiments, to the limitations of deep drawing processes, as discussed elsewhere in this application. These embodiments add opening 502 after the first die is removed from insertion through opening 504.

Figure 6:
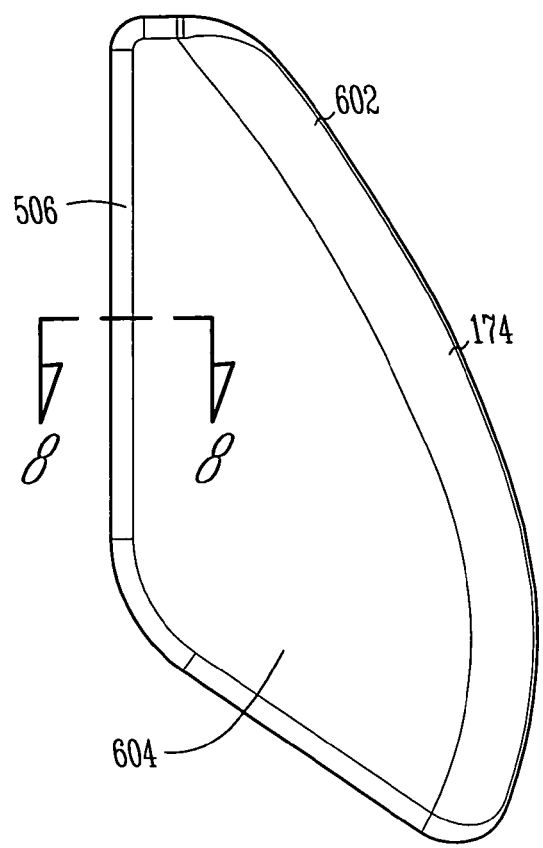
FIG. 6 is a front view of a capacitor case component, according to one embodiment of the present subject matter.

FIG. 6 is a front view of a capacitor case component, according to one embodiment of the present subject matter. The ergonomic shape of second shell 174 is visible. Various ergonomic designs include curves of varying profiles, including a short radius curve 506, and a long radius curve 602. Some curves are compound, comprising two or more radiuses. Wall portion 604 is a planar major surface, in various embodiments. In embodiments where second shell is purely curvilinear, such as ovoid embodiments, wall portion 604 does not exist.

Figure 7:
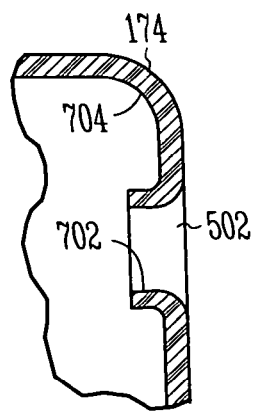
FIG. 7 is a cross section of a capacitor case component taken at line "7" in FIG. 5, according to one embodiment of the present subject matter.

FIG. 7 is a cross section of a capacitor case component taken at line "7" in FIG. 5, according to one embodiment of the present subject matter. Second shell 174 includes opening 502, in various embodiments. Opening 502 can serve as an electrical port, in various embodiments. The opening 502 is comprised of a wall which extends inward, to the volume partially defined by the interior wall 704 of second shell 174. As such, the opening is comprised of a face 702.

The shape of opening 502 can be the result of various manufacturing processes, as are known in the art. Punching, pressing, and otherwise forming second shell 174 can result in an opening 502, in various embodiments. One design feature present in various embodiments is face 702. Face 702, in various embodiments, protrudes into the interior defined by the capacitor shells 172, 174. A simple opening in the shells would result in a face which is approximately as thick as the shell. Face 702 extends into the shell farther than a simple opening. As such, embodiments using adhesive in a feedthrough benefit from the increased size of face 702. The increased size of face 702 improves bonding by enabling more adhesive to contact a surface, in various embodiments.

Figure 8:
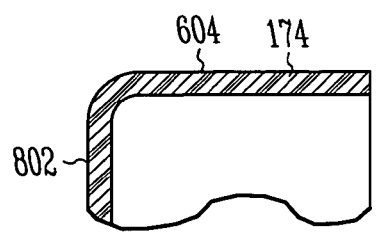
FIG. 8 is a cross section of a capacitor case component taken at line "8" in FIG. 6, according to one embodiment of the present subject matter.

FIG. 8 is a cross section of a capacitor case component taken at line "8" in FIG. 6, according to one embodiment of the present subject matter. The illustration presents one example profile of a shell. Wall 802 extends toward an edge, such as an edge used for mating second shell 174 to a mateable edge of first shell 172. Wall 604 comprises a major surface of embodiments of second shell 174 which have a rectangular cross section.

Figure 9:
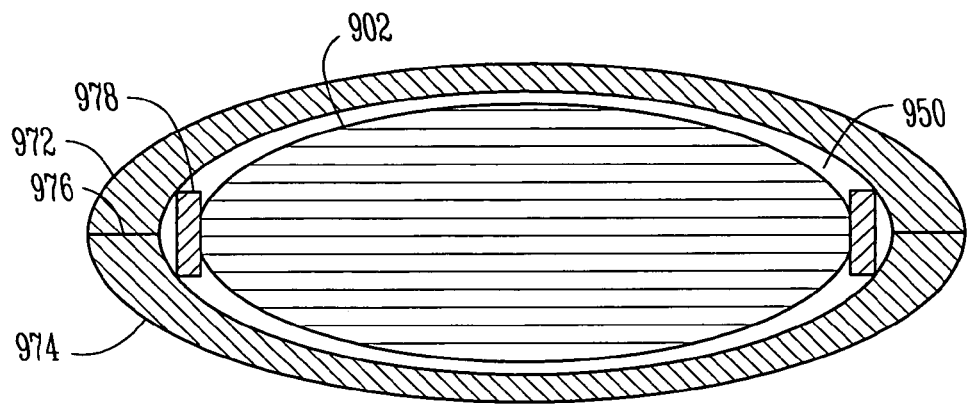
FIG. 9 is a cross section of a capacitor with two cupped shells, according to one embodiment of the present subject matter.

FIG. 9 is a cross section of a capacitor with two cupped shells, according to one embodiment of the present subject matter. The capacitor components illustrated include a capacitor stack 902, a first shell 972, and a second shell 974. Although the capacitor components comprise an ovoid cross section, other embodiments are within the scope of the present subject matter, including those with a rectangular cross section, or those with cross sections shaped otherwise. It is important to note that the present subject matter is not limited to symmetrical embodiments: asymmetrical embodiments are also within the scope of the present subject matter, and can be used to match specially shaped devices.

Various embodiments include a backing element 978. A backing element 978, in various embodiments, is used as a structural element of the capacitor. For example, if a backing element 978 is attached to one shell, it can be used in the alignment of a second shell. In embodiments in which the backing element 978 is welded to one of the first shell or the second shell, various configurations are possible. Some embodiments weld the backing element 978 to one shell, creating a step. Some embodiments create a weld which is flush with the exterior of the first shell 972 and the second shell 974. Additional embodiments create a weld which is not flush with the exterior of first shell 972 and second shell 974. Additional configurations not enumerated here are also within the scope of the present subject matter.

Backing element 978 is useful in joining processes for capacitor components, in various embodiments. For example, a backing element 978 can help reduce harmful effects of laser welding in embodiments using laser welding to seal joint 976, for example. Lasers used to connect shells 972, 974 along joint 976 can refract in various embodiments, and damage other capacitor components. A backing element 978 can reduce instances of refraction, reducing incidents of damage occurring during laser welding. Although backing element 978 is shown with a rectangular cross section, other embodiments are within the scope of the present subject matter. Additionally, while space 950 is present in the illustrated embodiment, it does not exist in other configurations. Combinations of capacitor stacks and shell shapes are adapted to eliminate spaces existing between a capacitor stack and a shell, in various embodiments.

In various embodiments, backing element 978 is attached to or incorporated with a capacitor stack. Some of these embodiments include incorporating backing element 978 into a covering for capacitor stack 902. For example, one of these embodiments includes a backing element 978 which is covered and constrained by a film form-fitted to the capacitor stack. Another example utilizes a form fitting film which has properties adapted to reduce damaging refraction. The present subject matter additional includes, but is not limited to, embodiments described in the following related commonly assigned copending U.S. patent application, incorporated herein by reference in its entirety: "Heat Shrinkable Wrap for Capacitor," Ser. No. 11/124,792, filed on May 9, 2005.

Figure 10:
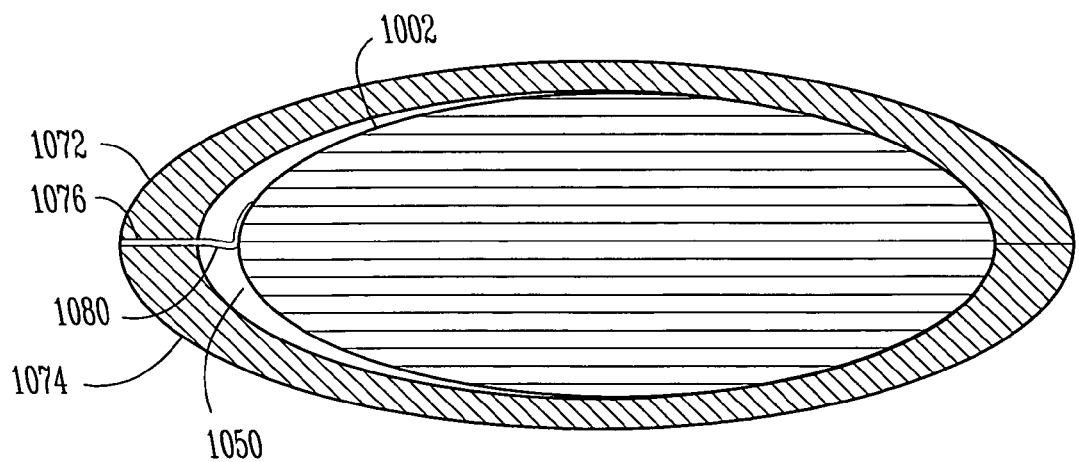
FIG. 10 is a cross section of a capacitor with two cupped shells, according to one embodiment of the present subject matter.

FIG. 10 is a cross section of a capacitor with two cupped shells, according to one embodiment of the present subject matter. The capacitor components illustrated include a capacitor stack 1002, a first shell 1072, and a second shell 1074. While space 1050 is present in the illustrated embodiment, it does not exist in other configurations, as they can include components sized to eliminate space 1050. Although the capacitor components comprise an ovoid cross section, other embodiments are within the scope of the present subject matter, including those with a rectangular cross section, or those with a cross section shaped otherwise. It is important to note that the present subject matter is not limited to symmetrical embodiments: asymmetrical embodiments are also within the scope of the present subject matter, and can be used to better match some patient anatomy.

Various embodiments including an interconnect 1080. An interconnect 1080, in various embodiments, is used to conduct electricity from the capacitor stack 1002 to components external to the capacitor. In some embodiments, an interconnect extends from the capacitor stack 1002 to one or more housing components, including shells 1072, 1074. In embodiments where one or more housing components are conductive, the interconnect 1080 connects the conductive housing component with the capacitor stack 1002. These embodiments include anodic case capacitors and cathodic case capacitors. Connecting the interconnect 1080 as such is accomplished using a laser weld, in some embodiments. However, connections between interconnect 1080 and capacitor subcomponents include additional embodiments, including additional welding embodiments such as sold-state welding embodiments.

In some embodiments, the interconnect 1080 extends to a joint 1076. Joint 1076 is defined by the intersection of housing components including shells 1072, 1074.

In some of these embodiments, the interconnect is ribbon shaped, and extends from capacitor stack 1002 to joint 1076 and outside of the capacitor. Some of these embodiments further trim the interconnect so that it is flush with the exterior of the capacitor housing. Interconnecting the anode or the cathode of capacitor stack 1002 to components external to the capacitor using embodiments having interconnect 1080 can reduce manufacturing complexity, and improve manufacturing efficiency.

Exemplary Embodiment of Implantable Defibrillator

Figure 11:
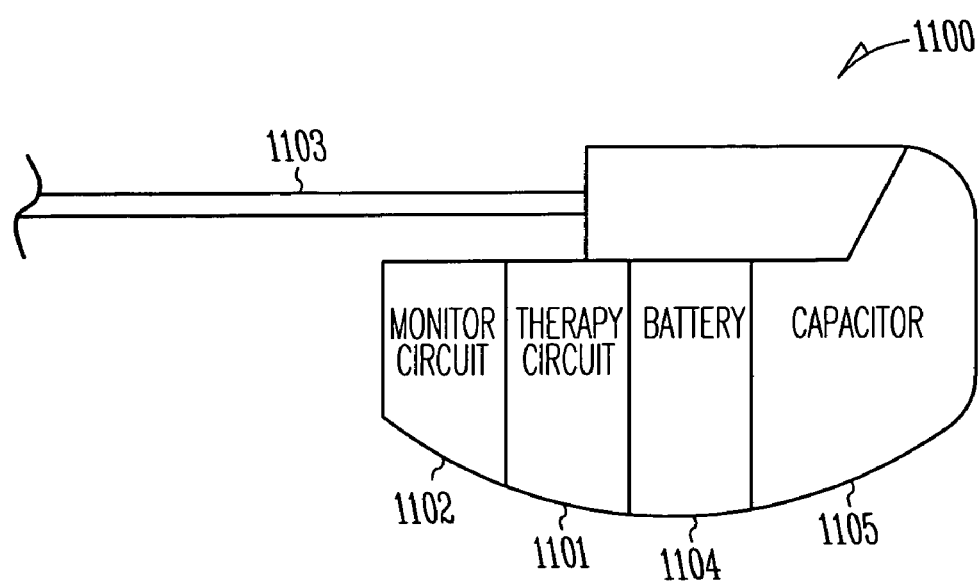
FIG. 11 is an example of a device having a capacitor of the present subject matter.

FIG. 11 shows one of the many applications for capacitors incorporating one or more teachings of the present subject matter: an implantable heart monitor or apparatus 1100. As used herein, implantable heart monitor includes any implantable device for providing therapeutic stimulus to a heart muscle. Thus, for example, the term includes pacemakers, defibrillators, cardioverters, congestive heart failure devices, and combinations and permutations thereof.

Heart monitor 1100 includes a lead system 1103, which after implantation electrically contact strategic portions of a patient's heart. Shown schematically are portions of monitor 1100 including a monitoring circuit 1102 for monitoring heart activity through one or more of the leads of lead system 1103, and a therapy circuit 1101 for delivering electrical energy through one or more of the leads to a heart. Monitor 1100 also includes an energy storage component, which includes a battery 1104 and incorporates at least one capacitor 1105 having one or more of the features of the exemplary capacitors described above.

In addition to implantable heart monitor and other cardiac rhythm management devices, one or more teachings of the present subject matter can be incorporated into cylindrical capacitors and/or capacitors used for photographic flash equipment. Indeed, teachings of the subject matter are pertinent to any application where high-energy, high-voltage, or space-efficient capacitors are desirable. Moreover, one or more teachings are applicable to batteries.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and various embodiments, will be apparent to those of skill in the art upon reviewing the above description. The scope of the present subject matter should be determined with reference to the appended claims, along with the full scope of equivalents to which such claims are entitled.

What is claimed is:

1. A capacitor, comprising:
 a first cupped shell having a first opening;
 a second cupped shell having a second opening, wherein the first opening and the second opening are adapted to sealably mate to form a closed shell defining a volume therein;
 a plurality of substantially planar capacitor layers in a stacked arrangement disposed within the volume; and
 an electrolyte disposed within the volume, the closed shell adapted to retain the electrolyte,
 wherein the closed shell includes one or more ports for electrical connections, and the plurality of substantially planar capacitor layers have a unpackaged energy density within a range from about 7.0 Joules per cubic centimeter of capacitor stack volume to about 8.5 Joules per cubic centimeter of capacitor stack volume.

2. The capacitor of claim 1, wherein the first cupped shell has a different profile than the second cupped shell.

3. The capacitor of claim 1, wherein the intersection between the first cupped shell and the second cupped shell is a lap joint.

4. The capacitor of claim 1, wherein the intersection between the first cupped shell and the second cupped shell is a butt joint.

5. The capacitor of claim 1, wherein the first cupped shell includes at least one of the one or more ports for electrical connection.

6. The capacitor of claim 5, wherein a joint defined by the intersection of the first opening and the second opening includes at least one of the one or more ports for electrical connections.

7. The capacitor of claim 1, further comprising:
 a backing element disposed between an intersection between the first cupped shell and the second cupped shell and the plurality of substantially planar capacitor layers.

8. The capacitor of claim 7, wherein the backing element is integrated with a binding film conformed to the plurality of substantially planar capacitor layers.

9. The capacitor of claim 1, further comprising:
 a first major surface of the first cupped shell, and a first wall extending between the first major surface and the first opening; and
 a second major surface of the second cupped shell, and a second wall extending between the second major surface and the second opening,
 wherein the first major surface and the second major surface are substantially parallel.

10. The capacitor of claim 9, wherein an edge surface defined by the first wall and the second wall is substantially continuous.

11. The capacitor of claim 10, wherein the first wall and the second wall define a substantially planar surface.

12. The capacitor of claim 10, wherein the edge surface is curvilinear.

13. The capacitor of claim 1, wherein the plurality of substantially planar capacitor layers have a packaged energy density within a range from about 5.3 Joules per cubic centimeter of capacitor stack volume to about 6.3 Joules per cubic centimeter of capacitor stack volume.

14. A capacitor, comprising:
 a plurality of substantially planar capacitor layers in a stacked arrangement;

a first shell means for partially housing the plurality of substantially planar capacitor layers;

a second shell means sealably mated to the first shell means at a joint and defining a closed shell means and further defining a volume therein, the closed shell means for housing the plurality of substantially planar capacitor layers; and electrolyte disposed within the volume, the closed shell means adapted to retain the electrolyte, wherein the plurality of substantially planar capacitor layers are disposed within the volume and the closed shell means includes one or more ports for electrical connections, and the plurality of substantially planar capacitor layers have a unpacked energy density of from about 7.0 Joules per cubic centimeter of capacitor stack volume to about 8.5 Joules per cubic centimeter of capacitor stack volume.

15. The capacitor of claim 14, wherein the first shell means has a different profile than the second shell.

16. The capacitor of claim 14, wherein an edge surface proximal the joint is substantially continuous.

17. The capacitor of claim 14, wherein the plurality of substantially planar capacitor layers have a packaged energy density within a range from about 5.3 Joules per cubic centimeter of capacitor stack volume to about 6.3 Joules per cubic centimeter of capacitor stack volume.

* * * * *

UNITED STATES PATENT AND TRADEMARK OFFICE
CERTIFICATE OF CORRECTION

| | | |
|---|---|---|
| PATENT NO. | : 7,075,777 B2 | Page 1 of 1 |
| APPLICATION NO. | : 11/124705 | |
| DATED | : July 11, 2006 | |
| INVENTOR(S) | : Doffing et al. | |

It is certified that error appears in the above-identified patent and that said Letters Patent is hereby corrected as shown below:

On the Title page, in Item (56), under "Foreign Patent Documents", in column 2, line 1, after "10/1990" insert -- H01G 9/00 --.

On the Title page, in Item (56), under "Other Publications", in column 2, line 3, delete "2005," and insert -- 2005 (Attorney Docket No. 279.829US1), --, therefor.

In column 1, lines 22–23, delete "Heat Shrinkable Wrap for Capacitor" and insert -- Method and Apparatus for Insulative Film for Capacitor Components --, therefor.

In column 8, lines 45–46, delete "Heat Shrinkable Wrap for Capacitor" and insert -- Method and Apparatus for Insulative Film for Capacitor Components --, therefor.

In column 11, line 14, in Claim 14, delete "unpacked" and insert -- unpackaged --, therefor.

Signed and Sealed this

Twentieth Day of November, 2007

JON W. DUDAS
*Director of the United States Patent and Trademark Office*